United States Patent [19]

Fleisher et al.

[11] Patent Number: 4,492,124
[45] Date of Patent: Jan. 8, 1985

[54] SAMPLING SYSTEM FOR STOOL ANALYSIS

[75] Inventors: Martin Fleisher, Glen Cove; Sidney J. Winawer, New York, both of N.Y.

[73] Assignee: Memorial Hospital for Cancer and Allied Diseases, New York, N.Y.

[21] Appl. No.: 404,201

[22] Filed: Jul. 30, 1982

[51] Int. Cl.³ .............................................. G01N 1/08
[52] U.S. Cl. .................................................. 73/864.44
[58] Field of Search .................. 73/864.44, 864.45; 128/749, 753, 754, 759; 422/58, 61; 436/66

[56] References Cited

U.S. PATENT DOCUMENTS

| Re. 27,637 | 5/1973 | Roach | 73/864.14 |
| 3,282,114 | 11/1966 | Pell | 128/759 |
| 3,783,998 | 1/1974 | Brush et al. | 128/749 |

FOREIGN PATENT DOCUMENTS 2607119  8/1977  Fed. Rep. of Germany ...... 128/749

Primary Examiner—S. Clement Swisher
Attorney, Agent, or Firm—Felfe & Lynch

[57] ABSTRACT

A sampling system for stool analysis provides an elongated handle and a cylindrical coring device, said handle including means for releasibly holding said coring device. The coring device is inserted into the stool to collect a representative sample. The sample is removed for analysis, as required.

9 Claims, 7 Drawing Figures

U.S. Patent   Jan. 8, 1985   4,492,124
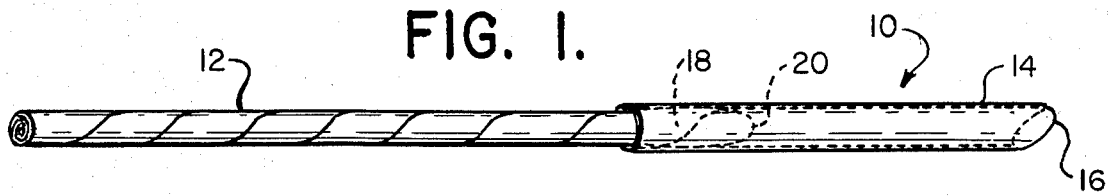
FIG. 1.
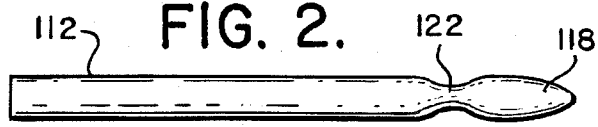
FIG. 2.
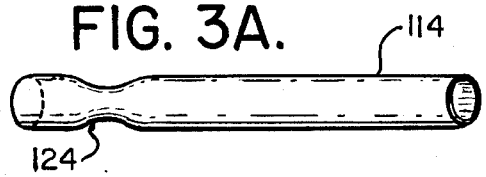
FIG. 3A.
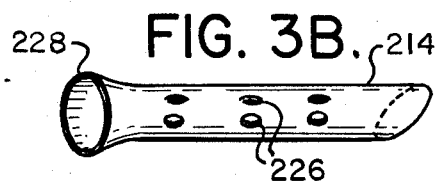
FIG. 3B.
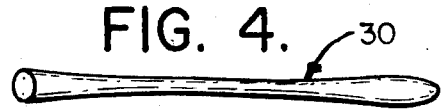
FIG. 4.
FIG. 5.
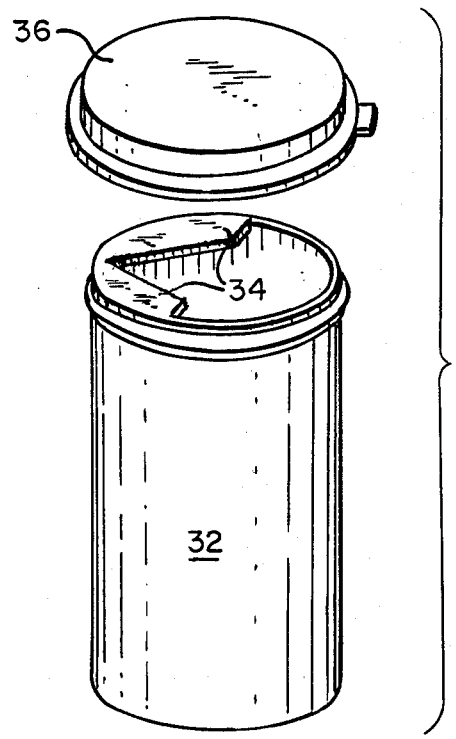
FIG. 6.
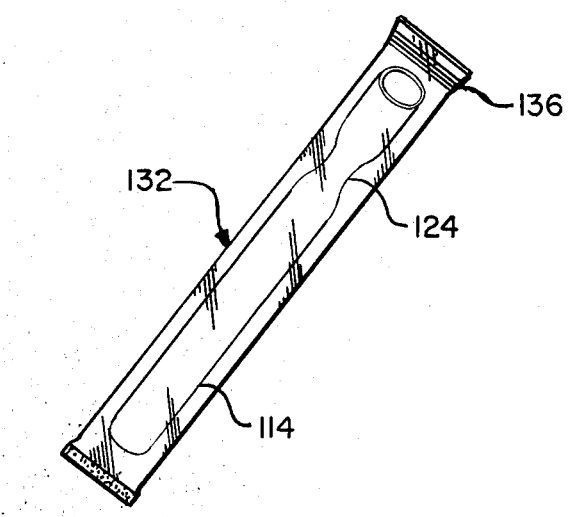

SAMPLING SYSTEM FOR STOOL ANALYSIS

BACKGROUND OF THE DISCLOSURE

The invention relates to a sampling system for stool analysis and method of use thereof.

For many diagnostic tests, it is important to obtain truly representative stool samples to ensure meaningful results. Diagnostic tests include chemical, parasitic and microbiological tests. Known tests permit detection and/or measurement of fecal occult blood; fats; bile and bile salts; porphyrines; parasitic agents; microbiological agents (bacteria etc); and drug and drug metabolites, for diagnostic and various other purposes.

Although the bases of most known analyses systems are sound, the sensitivity and reliability of these tests are dependent on proper specimen sampling. In most cases, specimen sampling is accomplished by the patient after the specimen has been deposited in a toilet. For example, the specimen can be scraped with a five inch wooden applicator, and smeared onto specially prepared chemically impregnated paper (slide) for use in fecal occult blood analysis. Even if the entire stool specimen is collected, sampling must still be done by a laboratory technician. Typically, the sample on the slide is covered with a paper flap which closes over the specimen, and the slide is sent through the mail or hand delivered to a laboratory or doctor's office for testing with guaiac or orthotolidine reagents for colorimetric hemoglobin determination. Many patients find this—and in fact all—stool sampling techniques requiring handling repugnant.

Prior sampling procedures have a number of disadvantages which are inherent therein. A primary disadvantage is that the sample collected is not necessarily representative of the entire specimen. Without a representative sample, the agent being detected may not appear or may appear at a non-representative concentration. For example, no blood may be detected by a fecal occult blood test even though it is present in the stool. A scraping sampling method requires that the blood or other agent in the stool be primarily on the surface of the specimen. However, if the agent is mixed into the feces far enough up in the digestive canal, it can be buried in the sample and not be available for sampling.

Other disadvantages include the question of hygiene for both the handlers of the sample and of the mail through which the sample is often sent to the laboratory for testing. Furthermore, the sampling method and the transmission to the laboratory through the mail on a slide, can result in damage to the sample itself if not properly protected. The sample can dry out or be degraded by atmospheric contaminants, especially humidity.

There is also the question of patient compliance in regard to collecting an appropriate specimen. As noted above, many patients find the collection instructions and procedure repugnant and will either not collect the specimen or incorrectly collect the specimen in any way they can get it over with. Poor patient compliance, i.e. improper sampling, obviates the clinical utility of various tests.

DESCRIPTION

The invention provides a means for obtaining a representative sample of the stool specimen to be tested. The device also provides a hygienic handling means for sampling the specimen, for transmission of the specimen to the laboratory where it is to be analyzed, and for handling in the laboratory itself.

In brief, the inventive sampling device comprises a cylindrical coring means which is provided with a separable handle. The sampling or coring means can be in a form of a cylinder of convenient length and having a suitable inside diameter for receiving a sample core. Preferably the cylinder has one end cut off at an angle to provide a piercing point. The handle may be a telescoping rod of flushable paper or other means which can be force-fitted into the back of the coring means or otherwise hold the coring means for hygienic handling thereof.

To sample the specimen, the coring means is pushed into the specimen to be filled with a core sample of the specimen. It is then removed from the specimen and released from the handle into a suitable container for transport and/or testing. The container may be sealed with a snap or screw cap or may have a self-closing sealing structure.

At the testing laboratory, testing solutions or a suitable suspending liquid can be added to the sample and the sample either analyzed directly therein or washed out of the coring device. The sample may also be pushed out with a suitable rod or otherwise dislodged and tested by any suitable means including the widely used paper-slide method. In the latter case the invention provides for proper sampling, adequate sample for multiple testing, and convenience of transportation to testing facilities.

If a sample bottle is used, this can be provided with a forked or wedge structure in the opening thereof to facilitate removing the coring device from the handle.

The handle can be formed of plastic, wood or any other suitable material but, as noted above, is most preferably of a swellable, flushable paper so that it can be disposed of with a minimum of effort and handling.

The coring device and the handle for use thereof can take a number of different forms including perforations formed through the walls to avoid air pressure build-up when sampling the specimen and to facilitate washing the sample from the coring device.

BRIEF DESCRIPTION OF THE DRAWINGS

In the drawings:

FIG. 1 is a perspective view of an assembled collection system according to the present invention;

FIG. 2 shows a modification of the handle to be used in assembling the collection system of the present invention;

FIGS. 3A and 3B show two coring devices in accordance with the collection system of the present invention;

FIG. 4 shows a sample removing device which may be employed for removing the sample from the coring device;

FIG. 5 shows a suitable sample bottle including forked or wedge structure in the opening thereof; and FIG. 6 shows a soft-walled mailing tube for for coring device.

With reference to FIG. 1, a collection system for occult blood assay 10 is shown with a handle portion 12 and a coring device portion 14. For convenience of handling and for sampling feces in a toilet bowl, a total device length at least of 8–10 inches is convenient. A longer device may be provided if this appears necessary because of patients' reluctance to take a sample. At about 2-3 feet the device becomes a little awkward for most people to handle for sampling and the removal of the coring device portion 14. The coring device 14 should be kept short for handling and shipping purposes. As can be seen in FIG. 1, an end of the handle 12 grips the coring device 14, preferably by being force-fitted into the rear of the coring device 14. The coring device is a cylinder, preferably round, for convenience of manufacture, and being at least 2 cm-10 cm long (approximately ¾ to 4 inches) and of 0.5-1.0 cm diameter. Although dimensions are not critical a coring device of about 4-8 cm is easily handled and shipped. To facilitate piercing the specimen, the front end of the coring device 14 may be cut at an angle to form a cutting point 16. The coring device 14 should also be made of water resistant material to avoid "wilting" during sampling if this is to be accomplished in a toilet bowl. Polyethylene is a convenient and readily available inert material for this purpose.

Handle 12, which may be about 2-3 (approx. 60-90 cm) feet long as indicated above, is preferable 5-50 cm long and most preferably 10-30 cms for handling convenience. Handle 12 is provided with front end 18 tapered at the tip 20 for easy entry into the rear of coring device 14. At least a portion near tip 20 is of sufficient size to be held by friction against the inside wall of the coring device 14. The handle 12 and coring device 14 may be supplied assembled or as separate pieces to be pushed together before use. For convenience of handling, the handle 12 is disposable and preferably formed of paper or other flushable or biodegradable material which can be flushed for easy disposal after use.

FIG. 2 shows another embodiment of the handle 112 wherein an indented area 122 is formed behind the front end 118. This provides a means for interlocking with a mating structure which can be formed in the coring device 114 (FIG. 3A).

FIG. 3A shows an embodiment of the coring device 114 which includes a suitable mating structure in the form of an indented area 124 near the rear end thereof. This coring device 114 is especially suitable for use with handle 112 as the indented area 122 of the handle 112 mates with the indented area 124 of the coring device 114. The front end tip may also be flat as illustrated at coring device 114.

FIG. 3B shows a further embodiment of the coring device 214. This embodiment 214 has perforations 226 formed through the wall thereof. The perforations 226 allow air to escape when a core is being taken from the specimen and also facilitate extracting the sample by providing a large exposed surface area. The rear end 228 of the coring device 214 is shown flared to facilitate handling in conjunction with wedge structure 34 as will be evident in the discussion of use presented below.

FIG. 4 shows a sample removal device 30 in the form of a rod like structure which can be inserted into the coring device 14, 114, 214 to push the sample out, if this method of handling is desired. The sample thus becomes available for various tests.

FIG. 5 shows a sample bottle 32 for containing the coring device 14, 114, 214. As can be seen in FIG. 5, the opening 34 in sample bottle 32 includes a wedge or forked structure 34. This facilitates removing the coring device 14, 114, 214 from the handle. One inserts the assembled collection system into the opening 34 of the sample bottle 32, wedges it between the arms of structure 34 and pulls up to dislodge the coring device 14, 114, 214 from the handle 12, 112. As is readily understood, the flared rear end 228 of the coring device 214 facilitates this by providing an enlarged portion against which the structure 34 can wedge. Once the coring device 14, 114, 214 is in the sample bottle, it is closed by closure 36, preferably a snap or screw closure.

Referring to FIG. 6, to provide for the convenience of mailing the core specimen a cylindrical soft plastic container 132 with press-close or other closure 136 can be substituted for the collection bottle 32.

The method of use of the collection system according to the present invention comprises assembling the handle 12, 112 and the coring device 14, 114, 214, by forcing the handle 12, 112 into the rear end of the coring device 14, 114, 214. The front end of the coring device 14, 114, 214 is then inserted into the stool sample, preferably with a slight twisting action whereby a core is taken of the sample. The coring device 14, 114, 214 is then dislodged by insertion into the bottle against the forked structure to be pulled free of the handle and allowed to fall into the bottle 32, or by inserting into soft plastic container 132, by gripping the container and pulling the coring device free of the handle. The handle is then disposed of or cleaned for reuse. The bottle 32 (or special mailing container 132) is closed with closure 36 (136) and mailed to the laboratory for analysis. At the laboratory, the sample is either removed, e.g. with the sample removal device 30 by pushing it through the coring device 14, 114, 214; or washing it from the coring device 14, 114, 214; or leaving it in the bottle 32 wherein a suspending liquid and other reagents may be added and the reaction take place.

Analysis of the sample can be accomplished by any usual procedure and is suitable for use with chemical, parasitic, and microbiological tests. Immunological test methods employing monospecific antibodies can be applied for difficult to detect agents such as drug and drug metabolites. This can be useful in detecting the presence and use of drugs, for example in police work as well as diagnostic purposes. These are even monospecific antibodies available which can detect the presence of hemoglobin although a sample obtained by the inventive device can be removed from the coring device and applied to a usual paper-impregnated test slide device or other slides for various presently more usual tests. This provides for a representative stool sample from different levels of the sample and of sufficient quantity for multiple tests or test runs.

It will be understood that the specification and examples are illustrative but not limitative of the present invention and that other embodiments within the spirit and scope of the invention will suggest themselves to those skilled in the art. Thus, for example, the entire specimen constituting a core sample from the coring device can be analyzed rather than a portion thereof e.g. for the presence of blood, by modified traditional methods including guaiac or orthotolidine or by an extraction procedure designed to remove fecal debris before testing for hemoglobin or other indicators of gastrointestinal bleeding. The specimen core may be used for immunochemical analysis by immunodiffusion techniques or immunoenzymatic reaction. Extraction of the specimen can be accomplished in the collection bottle or a test tube. It is furthermore obvious that other means can be used to releasably interconnect the handle and coring device, such as pincers or clamps.

What is claimed is:

1. A sampling system for stool analysis comprising an elongated handle and a cylindrical coring device, said handle including means for holding said coring device which comprises a structure operable to be force-fitted into said coring device.

2. The sampling system of claim 1 wherein said coring device includes a piercing tip.

3. A sampling system for stool analysis comprising an elongated handle and a cylindrical coring device, said handle including means for holding said coring device and said coring device having perforations defined through the wall thereof to facilitate sample removal.

4. The sampling system of claim 1 further comprising a sample bottle having a forked structure in the opening thereof, said forked structure cooperating with the coring device for separation thereof from the handle.

5. The sampling system of claim 1 wherein said coring device is a cylinder of about 2-10 cms long and the handle is a paper rod of about 10-30 cms long.

6. A feces sampling kit for obtaining a representative feces sample for testing comprising an elongated handle; a cylindrical coring device, said handle including means for holding said coring device which comprises a structure operable to be releasably force-fitted into said coring device.

7. The kit of claim 6 further comprising a collecting container comprising a sample bottle and means to facilitate removal of said coring device including a wedging structure formed in the opening of said bottle, said wedging structure being operable to wedge against said coring device to hold it and allow the handle to be withdrawn.

8. The kit of claim 6 further comprising a collecting container comprising a soft walled enclosure wherein the coring device may be received and held by manual gripping with the walls to allow removal of the handle.

9. Method of sampling feces comprising removably securing a handle to a feces sample coring device in the form of a tube inserting an end of the tube into the feces to fill the tube with a sample of the feces; withdrawing the tube from the sample; inserting the tube into a sample container; and removing the handle from the tube to leave the tube in the container.

* * * * *